United States Patent [19]

Chen et al.

[11] Patent Number: 4,866,167
[45] Date of Patent: Sep. 12, 1989

[54] DETECTION OF HUMAN ORAL CELLS BY NUCLEIC ACID HYBRIDIZATION

[75] Inventors: Michael C. Chen; Pearl M. Chen, both of Lexington; Lynn C. Klotz, Cambridge, all of Mass.

[73] Assignee: Biotechnica Diagnostics, Inc., Cambridge, Mass.

[21] Appl. No.: 769,565

[22] Filed: Aug. 26, 1985

Related U.S. Application Data

[63] Continuation-in-part of Ser. No. 707,054, Mar. 1, 1985, abandoned.

[51] Int. Cl.$^4$ .................... C07H 21/00; C12Q 1/68; C12Q 1/00
[52] U.S. Cl. ........................................ 536/27; 435/6; 435/29; 935/78; 436/811
[58] Field of Search ............... 435/6, 29, 803; 536/27; 436/63, 501, 811; 935/78

[56] References Cited

U.S. PATENT DOCUMENTS 4,358,535 11/1982 Falkow .
4,446,237 5/1984 Berninger .
4,458,014 7/1984 Ebersole .

FOREIGN PATENT DOCUMENTS 151536 8/1985 European Pat. Off. .

OTHER PUBLICATIONS

Biological Abstract 76 (1983) 15697 Van Steenbergen, T. J. M. et al. "DNA Homologies . . . and Related Species".
Biological Abstract 76 (1983), 42180 Tanner, A. C. R. et al. "Classification and Identification . . . DNA Hybridization".
Tanner et al., "Wolinella gen. nov., Wolinella Succinogenes (Vibrio succinogenes Wolin et al.) comb. nov., Description of Bacteriodes gracilis sp. nov., Wolinella recta sp. nov., Campylobacter concisus sp. nov., and Eikenella corrodens from Humans with Periodontal Disease," Int. Jour. of Sys. Bac., (1981), pp. 432–445.
Potts et al., "Relationships Among the Oral Fusobacteria Assessed by DNA–DNA Hybridization," Jour. of Dental Res. (1983) 62:702–705.
Tanner et al., "Classification and Identification of Antinobacillus actinomycetemycomitans and Haemophilus aphrophilus by Cluster Analysis and Deoxyribonucleic Acid Hybridizations," Jour. of Perio. Res. (1982) 17:585–596.
Van Steenbergen et al., "Confirmation of Bacteriodes gingivalis as a Species Distinct from Bacteriodes asaccharolyticus," Intern. Jour. of Systematic Bacteriology, (1981) pp. 236–241.
Coykendall et al., "Streptococcus mutan in a Wild, Sucrose-Eating Rat Population," Infection and Immunity, (1974) pp. 216–219.
Van Steenbergen et al., "Deoxyribonucleic Acid Homologies Among Strains of Bacteriodes melaninogenicus and Related Species", Jour. of Applied Bacteriology (1982) 53:269–276.
Slots et al. (1980) Infect. Immun. 29:1013–1020.
Mandell et al. (1981) J. Periodont. 52:593–598.
Tanner et al. (1979) J. Clin Periodont. 6:278–307.
Listgarten et al., (1979), J. Clin. Periodont. 5:115–132.
Keyes et al. (1983) JADA 106: 803–812.
Loesche et al. (1978) Infect. Immun. 21: 830–839.
Berninger et al. (1982) J. Med. Virol. 9: 57–68.
Brandsma et al. (1980) Proc. Natl. Acad. Sci. USA, 77:6851–6855.
Roberts et al. (1984) J. Clin. Micro. 20: 826–827.
Dent, V. E. et al., Int. J. Syst. Bact. vol. 34, 1984, pp. 316–320.
Meinkoth, J. et al., Anal. Biochem., vol. 138, 1984, pp. 267–269.
Kennell, D. E. In Progress in Nucleic Acid Research and Molecular Biology (Davidson, J. N. et al.) vol. 11, 1971, Academic Press, N.Y., pp. 259–261.
French, C. K. et al., Oral Micro Immunol 1:58–62 (1986).
Chen, M. et al., J. Dent. Res. 65 Abstract 1647, p. 352 (1986).
Savitt, E. et al., J. Dent. Res. 65 Abstract 1648, p. 352 (1986).

Primary Examiner—Johnnie R. Brown
Assistant Examiner—Jeremy H. Jay

[57] ABSTRACT

A probe for the detection, in a sample obtained from the mouth of a human patient, of a microbial or human cell associated with a human oral medical disorder, the probe consisting essentially of a segment of DNA or RNA capable of selectively hybridizing, under hybridizing conditions, to single-stranded DNA of the cell.

5 Claims, No Drawings

DETECTION OF HUMAN ORAL CELLS BY NUCLEIC ACID HYBRIDIZATION

This application is a continuation in part of Chen et al. U.S. Ser. No. 707,054, filed March 1, 1985 now abandoned.

BACKGROUND OF THE INVENTION

This invention relates to the diagnosis of human dental diseases and conditions by detection of microorganisms and cells associated therewith.

Dental diseases are quite prevalent in the United States and elsewhere. Perhaps 45 million adults suffer from destructive periodontal disease in the U.S., and perhaps 1 million children suffer from juvenile periodontitis. It can be estimated that 95% of the U.S. population suffers from dental caries at some point in life. There is a considerable need for diagnostic tools to allow a dentist to quickly and effectively detect the presence of these diseases and conditions, to aid and monitor treatment. This is especially true for juvenile periodontitis and dental caries, for which more specialized treatments exist.

Recent evidence suggests that different forms of periodontal disease have specific microbial etiologies. *Actinobacillus actinomycetemcomitans* has been well established to be a causative agent for juvenile periodontitis (J. Slots et al, Infect. Immun. 29: 1013–1020, 1980; Mandell and Socransky, J. Periodont. 52: 593–598, 1981). *Actinobacillus actinomycetemcomitans, Bacteroides, gingivalis, Bacteroides intermedius, Fusobacterium nucleatum, Capnocytophaga ochracea, Selenomonas sputigena, Eikenella corrodens, Wolinella recta*, spirochetes and fusiform Bacteroides are associated with, and implicated in the cause of, adult periodontal disease (Tanner et al., J. Clin. Periodont. 6:278–307, 1979; Dzink et al., J. Clin. Periodont. 9: in press 1985). In addition, leukocytes (white blood cells) are known to be present in periodontal pockets from patients suffering from periodontal disease (Listgarten & Hellden, J. Clin. Periodont. 5: 115, 1979; Keyes & Rams, J. Amer. Den. Svc. 106: 803, 1983). The presence of elevated levels of *Streptococcus mutans* in saliva samples is known to indicate a susceptibility to caries. (W. J. Loeche, et al., Infect. Immun. 21: 830, 1978).

One approach in diagnosing these medical disorders is to identify causative microorganisms by culturing and taxonomic identification of bacteria from samples from periodontal pockets. This approach is labor-intensive, and samples must be quickly and correctly handled to preserve their viability. Alternatively, assays for enzyme activities thought to be associated with causative organisms may be used. Various assays involving polyclonal or monoclonal antibodies have also been used. For example, Ebersole, U.S. Pat. No. 4,458,014, discloses a method for the serological identification of certain microorganisms from the oral cavity, in particular, black-pigmented Bacteroides. This method involves the preparation of polyclonal antibodies directed at these organisms by injection of killed cells into a mammal such as a rabbit, and recovery of antibodies from the mammal's serum. The polyclonal antibodies are used in a diagnostic protocol to detect organisms.

SUMMARY OF THE INVENTION

In general, the present invention features detecting, in a sample (e.g., saliva, a subgingival plaque sample obtained from a periodontal pocket, or a supragingival plaque sample) obtained from the mouth of a human patient, a microbial or human cell associated with a human oral medical disorder, by denaturing the DNA of the sample, contacting the denatured DNA, under hybridizing conditions, with probe RNA or DNA capable of selectively hybridizing to the denatured DNA of the cell, and detecting hybrid complexes as an indication of the presence of the cell in the sample.

The invention is particularly useful for the detection of *Actinobacillus actinomycetemcomitans* (which recently has been proposed to be reclassified as *Haemophilus actinomycetemcomitans* comb. nov. [Potts et al., J. System. Bact. 35: 337, 1985]), a causative agent of juvenile periodontitis, and *Streptococcus mutans*, associated with susceptibility to dental caries. The invention can also be used to detect other microbial and human cells associated with human oral medical disorders.

The method of the invention is highly sensitive, permitting the detection of only $10^3$ cells in a sample, and is also highly specific; cross-hybridization to DNA of other cells in the sample is less than 0.1% of hybridization to the cell being detected. In addition, detection is rapid, giving results in one to two days.

Other features and advantages of the invention will be apparent from the following description of the preferred embodiments thereof, and from the claims.

DESCRIPTION OF THE PREFERRED EMBODIMENTS

Preparation of Probes

Probe DNA or RNA can be prepared by any of several techniques, including purification and labelling of total cellular DNA of the cell to be detected (the "whole genome" method); the isolation of specific sequence probes from a library of the DNA of the cell to be detected; or the preparation of specific sequence RNA probes.

Whole Genome Probes

We have found that the total DNA of the cell to be detected can be labelled and used as a probe to detect oral disorder-associated cells. Such probes were found to be capable of detecting the presence of the key diagnostic organisms *A. actinomycetemcomitans* and *S. mutans* in oral samples, and were also successful in detecting *Bacteroides intermedius, Bacteroides gingivalis, Fusobacterium nucleatum, Eikenella corrodens, Wolinella recta*, and *Selenomis sputigena*.

Obtaining Cells

The first step in the preparation of whole genome probes is the preparation of a pure culture of microbial or human cells from which the whole genome probe is to be prepared; the cells are of the same species or type as the cell to be detected.

Any desired species can be isolated and purified from oral samples, and then cultured, using standard microbiological methods. In addition, some species of interest are publicly available, e.g., *A. actinomycetemcomitans* (ATCC Nos. 29522, 29523, 29524); *B. intermedius* (ATCC No. 25611); *W. recta* (ATCC 33238); *S. mutans* (ATCC 25175, 27351, 27352); *B. gingivalis* (ATCC No. 33277); *F. nucleatum* (ATCC No. 25586); and *E. corrodens* (ATCC No. 23834).

The following were obtained from Dr. Anne Tanner and Ms. JoAnn Dzink of the Forsyth Dental Center, Boston, Massachusetts: *Actinobacillus actinomycetemcomitans* strain Y4; *Bacteroides intermedius* 581; *Bacteroides gingivalis* 381; *Fusobacterium nucleatum* 364; *Eikenella corrodens* 373; *Wolinella recta* 371; *Capnocytophaga ochracea* 6; *Selenomonas sputigena* 1304; and *Streptococcus mutans* JBP.

These microorganisms were cultured according to published procedures (Dzink et al., J. Clin. Micro. 19: 599, 1984), harvested and centrifuged to form a cell pellet, and lyophilized. Total cellular DNA was extracted from 0.1 gm of lyophilized cells by the following method. The cells were resuspended in 20 ml of TES buffer (10mM Tris-HCl; 100mM NaCl; 1mM EDTA, pH 8.0), centrifuged for 10 minutes at 8000 rpm (5000×g), and the supernatant was discarded. The pellet was then resuspended in 10 ml of TES buffer containing 25% sucrose, for cell lysis.

For gram-positive organisms (e.g., S. mutans), 5 mg of N-acetylmuramidase (Miles Labs) was added to the 10 ml lysis mixture. For gram-negative organisms (e.g., all the others listed above), 5 mg of lysozyme (Sigma) was added to the 10 ml of the lysis mixture. In those cases where the classification of the organism is not known, or with certain gram-negatives such as *B. gingivalis*, both enzymes may be added. Treatment with either enzyme was done for 30 minutes at 37° C.

Following this incubation, 0.8 ml of 25% w/v sodium lauryl sulfate and 0.5 ml pronase (Sigma) were added, and the mixture was incubated for 30 minutes at 70° C. The mixture was then cooled on ice, 2.8 ml of 5 M sodium perchlorate was added, mixed well and incubated on ice for 15 minutes. 15 ml of cold chloroform: isoamyl alcohol (24:1 v/v) was added. After mixing, the mixture was left on ice for 15 minutes. The mixture was centrifuged at 6000 rpm (2800×g) for 10 minutes. The aqueous phase was removed with a wide-mouthed pipet, and centrifuged for 10 minutes at 12,000 rpm (11,200×g). The supernatant was collected, chilled on ice for 15 minutes, and 2 volumes of 95% ethanol were added. After 30 minutes on ice, the mixture was centrifuged at 8000 rpm (5000×g) for 15 minutes, and the supernatant was discarded.

After drying, the pellet was resuspended in 1 ml of TE buffer (10mM Tris HCl, 1mM EDTA, pH 8.0). 50 microliters of 10 mg/ml RNase was added (RNase, obtained from Sigma, dissolved in 10mM Tris pH 7.5, 15mM NaCl, was prepared in advance by heating at 100° C. for fifteen minutes, slow cooling, dispensing into aliquots for storage at −20° C.). The RNase reaction was carried out at 37° C. for one hour.

Following RNase treatment, 2-3 extractions were done with phenol: chloroform: isoamyl alcohol (49:49:1), and the aqueous phase was collected. 2 ½ volumes of 100% ethanol were added, with 1/10 volume of 3M sodium acetate (pH 5.5). After 30 minutes on ice, the mixture was centrifuged for 10 minutes at 8000 rpm (5000×g). The pellet was washed twice with 70% ethanol, dried and resuspended in 1 ml of TE buffer. The concentration of DNA was measured by $OD_{260}$.

Human white blood cells were isolated from defibrinated treated blood through Ficoll-plaque (Pharmacia) according to the protocol provided by the manufacturer, and DNA was isolated according to the procedure described in Methods of Enzymology 65: 410, 1980.

Nick-Translated Whole Chromosome Probes

Preparations of total cellular DNA can be labelled by nick-translation by any standard method, including the following. The procedure described below incorporates $^{32}P$-labelled nucleotides into the nick-translated DNA as the label; however, other labelled nucleotides are acceptable substrates for DNA polymerase I in the nick translation reaction. Examples of such a label are the biotin-labelled analogs of dUTP described in Langer et al. (Proc. Nat. Aca. Sci. 78: 6633, 1981). Other examples include any molecule (e.g., a fluorescently labelled nucleotide) which can be incorporated by DNA polymerase I into a polynucleotide, without significantly affecting duplex stability or the kinetics of duplex formation.

One to two micrograms of bacterial or white blood cell DNA (from the species listed above), prepared as described above, was added to a reaction mix comprising 5 ul 10x buffer (0.5 M Tris-CHl, pH7.2; 0.1 M $MgSO_4$, 1mM dithiotreitol, and 500 ug/ml bovine serum albumin); 4 ul unlabelled deoxynucleotides (10 um dATP, 100 um each dCTP, dGTP, dTTP); 30 ul $\alpha$-$^{32}P$-dATP (2800 Ci/mmol); and distilled $H_2O$ to 48 ul. This mixture was chilled to 0° C., and 1 ul of DNase (Sigma: 0.1 ug/ml) and 1 ul of *E. coli* DNA polymerase I (Boehringer Mannheim: 5 units/ml) were added. The reaction was incubated at 16° C. for one hour, and was stopped by adding 2 ul of 0.5 M EDTA, and then 50 ul of distilled $H_2O$ was added. The labelled nick-translated DNA was separated from unincorporated label by centrifugation through a Sephadex G50 column in a 1-ml syringe. Labelled DNA preparations may be stored at −20° C. before use.

DNA Libraries for Specific Sequence Probes

Alternately, one can prepare nucleic acid probes by constructing cloned DNA libraries representing all the DNA sequences of a given organism. Procedures to prepare DNA libraries and label the nucleic acid sequences are described below. Any individual nucleic acid sequence having homology to the target organism or cell, and lacking homology to other oral microorganisms or cells, may be a suitable probe for the target cell. Many such sequences are presumed to be present in the libraries prepared as described below, or in other libraries that may be similarly prepared. Any such sequence may be identified and isolated from within a DNA library, e.g., through differential hybridization assays such as the one described below. Such sequences may be used singly or in combination, and it is also possible to use the entire library as a probe.

Specific Sequence Probes: DNA Probes

Single-stranded libraries of DNA from the above-listed organisms and cells can be prepared using M13 phage as a vector. The following example, using *A. actinomycetemcomitans*, *S. mutans* and *S. sputigena*, is illustrative of this procedure. DNA from the replicating form of phage M13 (M13 RF mp 7; Messing et al., Nucl. Acids Res. 9:309, 1981; obtained from P-L Biochemicals) was digested with BamHl to give a linear double-stranded DNA molecule with GATC cohesive ends. Purified bacterial DNA, prepared as described above, was digested with Sau3A, yielding fragments with cohesive ends complementary to the M13 sticky ends. The restricted bacterial DNA was mixed with the M13 DNA, the mixture ligated and used to transfect competent E. coli strain JM107 at a 10:1 molar ratio, and ampicillin resistant colonies were selected for.

The DNA inserts at the BamHI site will disrupt normal expression of the lacZ gene carried by this strain of the phage. M13 molecules carrying inserts at this site will be unable to express beta-galactosidase from the lacZ gene, and thus will give colorless plaques when grown on plates containing 5-bromo, 4-chloro, 3-indoyl, beta-D-galactoside (X-gal). This allows clones carrying inserts to be distinguished from those that do not, which produce blue plaques on X-gal plates.

M13 single-stranded DNA molecules carrying bacterial DNA inserts are purified from E. coli cells by the method described in Methods in Enzymology 101:20; 1983. The $^{32}$P-labelled M13 probes were prepared as follows. The M13 single-stranded DNA was annealed to a synthetic DNA primer of the sequence 3'CAACA-CACCTTAACAC 5', in a reaction mix consisting of 20 ul of M13 single-stranded DNA (50 gm/ul), 12 ul of primer (20ng/ul), 5 ul of 10x annealing buffer (10mM Tris-HCl pH 7.5, 500 mM NaCl, 100mM DTT, 100mM MgCl$_2$) and 8 ul of distilled H$_2$O. The mixture was heated to 100° C. and slowly cooled to room temperature in a one hour period. After annealing, the mixture was added to 25 ul of $\alpha$-$^{32}$P-dATP (3200 Ci/mmol) 20 ul of 10 uM dATP, 100 uM each of dGTP, dCTP, dTTP, 5 ul of 10x annealing buffer, 2 ul of DNA polymerase (large fragment) (4 unit/ul). The mixture was incubated at room temperature for two hours. The reaction was stopped by adding 10 ul of 0.25M EDTA, and the $^{32}$P-labelled M13 probe was then separated from unincorporated $^{32}$P-dATP by centrifugation through G50 Sephadex in a 1-ml syringe.

Specific Sequence Probes: RNA Probes

Bacterial DNA libraries from the above listed organisms and cells can be prepared using pSP64 as a vector. The following example, using A. actinomycetemcomitans, S. mutans, S. sputigena, B. intermedius, B. gingivalis, F. nucleatum, E. corrodens, W. recta, C. ochracea, and white blood cells, is illustrative of this procedure. The plasmid pSP64, obtained from Promega Biotec, was digested with BamHI to give a linear double-stranded DNA molecule with GATC cohesive ends. Purified bacterial DNAs, prepared as described above, were digested with Sau3A, yielding fragments with cohesive ends complementary to the pSP64 cohesive ends. The restricted bacterial DNA was mixed with the pSP64 (10:1 molar ratio), the mixture ligated and used to transform competent E. coli HB101 and select for ampicillin resistant colonies.

In order to verify that the bacterial DNA had inserted into pSP64, 20 clones from each bacterial library were randomly selected. The plasmids were purified and digested with EcoRI and PstI, to detect the presence of inserts by restriction mapping.

$^{32}$P-labeled RNA probes from each DNA library were prepared by linearizing plasmids containing inserts with EcoRI, and transcribing this DNA according to the following method, provided by Promega Biotec. Transcription took place in a 50 ul reaction consisting of: 10 ul 5×buffer (200mM Tris-CHl; 30 mM MgCl$_2$; 10mM spermidine); 9 ul distilled H$_2$O that had been treated with diethylpyrocarbonate; 0.5 ul 1 M dithiotreitol; 2 ul RNasin TM ribonuclease inhibitor (30 U/ul); 5 ul 5mM each GTP, CTP, ATP; 2.5 ul 0.125mM UTP; 10 ul DNA from pSP64 clones (5ug/50; ul); 10 ul $\alpha$-$^{32}$P-UTP (3000 Ci/mmol); 1 ul Riboprobe TM RNA polymerase (15 U/ul). Incubation was for one hour at 40° C. After this reaction, 1 ul of DNase (1 mg/ml) and 1.8 ul of RNasin TM (30 U/ul) were added, and the mixture was incubated 10 minutes at 37° C. 100 ul of distilled H$_2$O was added, the solution was phenol-extracted twice, and the aqueous phase was centrifuged through G50 Sephadex that had been equilibrated in 10 mM Tris, pH 7.0; 1 mM EDTA; 0.1% SDS.

The biotin-labelled analogs of UTP described by Langer et al., id may be used as an alternate label.

Selection of Specific Probes from DNA Libraries

Specific nucleic acid sequences may be selected from the cloned DNA libraries for use as probes. Desirable sequences are those that show strong hybridization to the target cell while showing little or no non-specific reactivity to non-target cells. Such sequences may be selected by any differential hybridization assay. The below-described procedures, in which probe candidates are selected from the DNA libraries of three organisms, and from the RNA library of one organism, are illustrative of procedures that may be used to select probe candidates for any number of organisms.

The M13 libraries of A. actinomycetemcomitans, S. mutans and S. sputigena were screened to identify clones showing no cross-reactivity to the other two organisms. From each library, 50 E. coli clones harboring insert-containing M13 were grown separately in 1-ml Eppendorf tubes, and several microliters of whole E. coli cells from each clone were spotted and fixed onto duplicate nitrocellulose filters, so that each filter contained 50 spots, representing only clones from the library of a single organism. Spotting is done by applying one to two microliters of cell suspension to the filters with a micropipette and air-drying for approximately 30 minutes. For each library to be screened, two preparations of total cellular DNA were prepared: (a) "target cell" DNA; (b) pooled DNA from the two other, "non-target" cells. These preparations were nick-translated with a $^{32}$P label as described above, and each incubated for hybridization to one of the duplicate filters, by any standard hybridization procedure, including the one described below. Any clone showing hybridization to the pooled "non-target" DNA is not a suitable probe. Any clone showing little or no hybridization to the "non-target" DNA while hybridizing well to "target" DNA, is a suitable candidate for a probe. Using this procedure, approximately 20 individual M13 clones were identified as probe candidates from each of the libraries of A. actinomycetemcomitans, S. mutans and S. sputigena.

A. actinomycetemcomitans shares some biochemical and genetic similarities with Haemophilus aphrophilus and H. paraphrophilus (Tanner et al. J. Periodont. Res. 17:585, 1982; Potts et al., id.), which are sometimes present in the dental flora. Our whole-genome probes to A. actinomycetemcomitans showed significant cross-reactivity to cells of these Haemophilus species, a result in agreement with DNA—DNA hybridization studies reported in Potts et al., id. We therefore chose to select specific A. actinomycetemcomitans pSP64 clones which exhibit minimal cross-reactivity to H. aphrophilus and H. paraphrophilus.

One hundred individual E. coli clones from the A. actinomycetemcomitans pSP64 library were screened by the method described above. These clones were grown separately in 1-ml Eppendorf tubes, and several microliters of whole E. coli cells from each clone were spotted and fixed in duplicate onto nitrocellulose filters. Spotting was done by applying one to two microliters of cell suspension to the filters with a micropipette and air-drying for approximately 30 minutes.

Two separate preparations of total cellular DNA were prepared: (a) *A. actinomycetemcomitans* DNA; (b) pooled DNA from *H. aphrophilus* and *H. paraphrophilus*. These preparations were nick-translated with a $^{32}$P label as described above, and each incubated for hybridization to one set of filters, by the hybridization procedure described below. Several pSP64 clones were selected which hybridized to *A. actinomycetemcomitans* DNA but not to *H. aphrophilus* or *H. paraphrophilus* DNA. Of these, five clones (numbers 154, 157, 198, 200 and 207) were chosen as those exhibiting the best specificity.

$^{32}$P-labeled RNA from these five clones were prepared as described above. Whole cells from *A. actinomycetemcomitans* (strains Y4, 511, 652, ATCC 29522, ATCC 29523, ATCC 29524, 650, 651, 652, 2043, 2097, 2112, N27, NCTC 9710); *H. aphrophilus* (strains 621, 626, 654, 655, H77, H80, H81, ATCC 13252, ATCC 19415, NCTC 5906); *H. paraphrophilus* (strains H76, H78, ATCC 29241) and *H. influenza* (strains H9, H104) were each spotted onto five nitrocellulose filters as described above. $^{32}$P-labeled RNA from the five clones were separately hybridized to the filters by the method described below. Each of the five specific *A. actinomycetemcomitans* RNA probes hybridized strongly to cells of *A. actinomycetemcomitans*, and showed no significant hybridization above background to any of the Haemophilus cells. Representative specific clone number 198 in *E. coli* (designated *E. coli* K12/pSP64-Aa198) has been deposited in the American Type Culture Collection, and has been given ATCC Accession No. 53219. Applicants' assignee, BioTechnica International, Inc., acknowledges its responsibility to replace this culture should it die before the end of the term of a patent issued hereon, and its responsibility to notify the ATCC of the issuance of such a patent, at which time the deposit will be made available to the public. Until that time the deposit will be made available to the Commissioner of Patents under the terms of 37 CFR ≳1.14 and 35 USC ≳112.

Preparation of Probes for Diagnostic Use

Probes, whether representing single sequences, combinations of sequences, or whole libraries, can be synthesized on a large scale by the recombinant DNA methods described above. Single-sequence DNA probes or combinations thereof can instead be synthesized chemically, using conventional methods and/or automated equipment, providing the nucleotide sequence has been determined by any of the conventional sequencing methods.

Probes, in sufficient amounts for practical diagnostic use, may be prepared and labelled as described herein. Alternatively, either nucleic acid may be labelled after synthesis by attaching the label by chemical or biochemical methods. If $^{32}$P is the label, probes should be used within about two weeks of synthesis, due to the short half-life of the isotope.

DETECTION OF CELLS IN CLINICAL SAMPLES

In diagnostic procedures to detect periodontal diseases, plaque samples must be obtained from the patient's mouth. Plaque samples from periodontal pockets may be obtained using any of the standard plaque retrieval methods, using periodontal curettes or other dental instruments. Alternatively, specialized sampling instruments, such as the modified barbed broach described by Newman et al. (J. Periodont. 47: 373, 1976), may be used. We have also found paper points to be useful in removing plaque samples from periodontal pockets.

In any case, the plaque sample is removed from the mouth and placed into a solution such as Ringer's solution for dispersal of trapped bacteria. Dispersal is done under aseptic conditions, by sonic oscillation for no more than 10 seconds, or by vortexing. The sample can then be diluted and a portion of the sample is used for the hybridization reaction. Plaque samples are first treated with N-acetylmuramidase as described above, or other enzymes which promote cell lysis, and then are spotted and fixed onto nitrocellulose filters by applying one to two microliters of cell suspension on to the filters with a micropipette and air-drying for approximately 10 minutes.

In diagnostic procedures to detect caries susceptibility, *S. mutans* may be detected in plaque samples or in the patient's saliva. The usual procedure for drawing saliva involves collecting the saliva after the patient has chewed paraffin, which increases the amount of saliva produced and increases the shedding of *S. mutans* from the teeth. Saliva is then blotted onto filter paper for the hybridization reaction.

Hybridization to the labelled probes is conducted according to standard procedures [e.g., as described in Falkow et al. U.S. Pat. No. 4,358,535, and Roberts et al. (1984) J. Clin. Micro. 20, 826, both hereby incorporated by reference], and hybrid complexes detected by autoradiography or by other assay methods (e.g., fluorescence). A positive test for a given organism occurs when significant bound radioactivity or other label is detectable on the filter. One hybridization method is carried out as follows. Whole chromosome probes are denatured by treatment at 100° C. for 5 minutes, and immediately put on ice water before hybridization. This step is not necessary for RNA and M13 probes. In DNA—DNA hybridizations, the DNA in the filter-bound samples is denatured by soaking in 0.5M NaOH, 1.5 M NaCl for 5 minutes, followed by neutralization with 1.5 M NaCl 0.5 M Tris-HCl pH8.0 for 5 minutes. Hybridizations are done according to Denhardt (Biochem. Biophys. Resp. 23: 641; 1966), except that washes after 16 hours of hybridization are performed at 65° C. with 1×SSC plus 0.1T SDS, followed by three washes with 0.1×SSC+0.1% SDS.

DNA-RNA hybridizations are carried out as follows: After blotting, the nitrocellulose filters are baked in a vacuum for two hours at 80° C., and then prehybridized at 42° C. for 4 hours in the following buffer: 50% formamide; 50 mM Na phosphate (pH 6.5); 0.8M NaCl; 1 mM EDTA; 0.1% SDS; 0.05% BSA; 0.05% Ficoll; 0.05% PVP; 250 ug/ml denatured salmon sperm DNA; 500 ug/ml yeast RNA; +/− poly A at 10 ug/ml. The hybridizations are done in fresh buffer (as above) with the addition of probe, at 42° C. with 50 mM NaCl; 20mM Na phosphate (pH 6.5); 1mM EDTA; 0.1% SDS.

The exposure time of the autoradiography is determined by the amount of radioactive label present. Longer exposure times, while enhancing the signal for the cell to be detected, also increase the amount of signal for non-specific background hybridization.

Therefore, exposure times should be chosen with this in mind. Times of 2-6 hours are typical.

Other Embodiments

Other embodiments are within the following claims. The methods of this invention are useful for the detection of any microorganism or other cell present in the human mouth, for the diagnosis of any dental disease or condition. Examples of other diseases and the microorganisms associated with them are chronic gingivitis: *Fusobacterium* species, *Campylobacter* species, *B. intermedius, Bacterionema matruchoti*; alveolar bone loss: for example, *Actinomyces naeslundii, Nocardia* species; acute necrotizing ulcerative gingivitis (trenchmouth): *Fusobacterium* species, *B. intermedius*, spirochetes. It is also possible to use this invention to detect microorganisms associated with healthy gingiva, for example, *Streptococcus sanguis, Streptococcus mitis, Actinomyces viscosus* and *Veillonella* species.

Cloned DNA libraries of oral organisms and cells may be prepared by alternate methods. Libraries may be prepared using other restriction enzymes, particularly those that cut the target genome to an average size of 100 to 500 nucleotides. Other single-stranded DNA phages are potential cloning vectors, including $0 \times 174$ and Fd. Any of the common double-stranded DNA vectors (e.g., pBR322) may also be used to prepare libraries. RNA probes may also be prepared using PT7 vectors. Other host organisms may be used for DNA libraries, but *E. coli* is preferred due to the ease of cloning in this organism.

Different unique sequence molecules may be combined to form probes, the number of such seqences combined dependent upon needed specificity of sensitivity. Probes for different organisms and/or serotypes can be combined to obtain diagnostics more useful to the dental practitioner.

Hybridization conditions may vary from those disclosed here. In particular, probe nucleic acid may be contacted with sample DNA in any of several different ways, including the "sandwich" method of Ranki U.S. Pat. No. 4,486,539. Finally, other detection methods are possible, including incorporated labels (e.g. nucleotide analogs attached to biotin or fluorescent labels) or labels that are added to the nucleic acid after synthesis (e.g., fluorescent labels, enzyme-activity-based labels, etc.).

We claim:

1. A probe for the detection, in a sample obtained from the mouth of a human patient, of Actinobacillus actinomycetemcomitans, said probe consisting essentially of an isolated segment of DNA or an RNA complement thereof capable of stably and selectively hybridizing, under hybridizing conditions, to single-stranded DNA of Actinobacillus actinomycetemcomitans.

2. The probe of claim 1 wherein said probe is capable of detecting $10^3$ of said cells in said sample.

3. The probe of claim 1 wherein said human patient has juvenile periodontitis.

4. The probe of claim 1 wherein said probe DNA or RNA is a cloned DNA fragment or an RNA complement thereof.

5. The probe of claim 1 wherein said human patient has adult periodontal disease.

* * * * *

UNITED STATES PATENT AND TRADEMARK OFFICE
CERTIFICATE OF CORRECTION

PATENT NO. : 4,866,167

DATED : September 12, 1989

INVENTOR(S) : Michael C. Chen et al.

It is certified that error appears in the above-identified patent and that said Letters Patent is hereby corrected as shown below:

Column 1, line 42, "SVC" should be --Soc.--.

Column 4, line 19, "Tris-CHl" should be --Tris-HCl--.

Column 5, line 62, "Tris-CHl" should be --Tris-HCl--.

Signed and Sealed this

Twenty-eighth Day of April, 1992

Attest:

HARRY F. MANBECK, JR.

*Attesting Officer*     *Commissioner of Patents and Trademarks*